Dec. 3, 1968 D. L. ARMSTRONG Plant Pat. 2,849
ROSE PLANT
Filed June 14, 1967
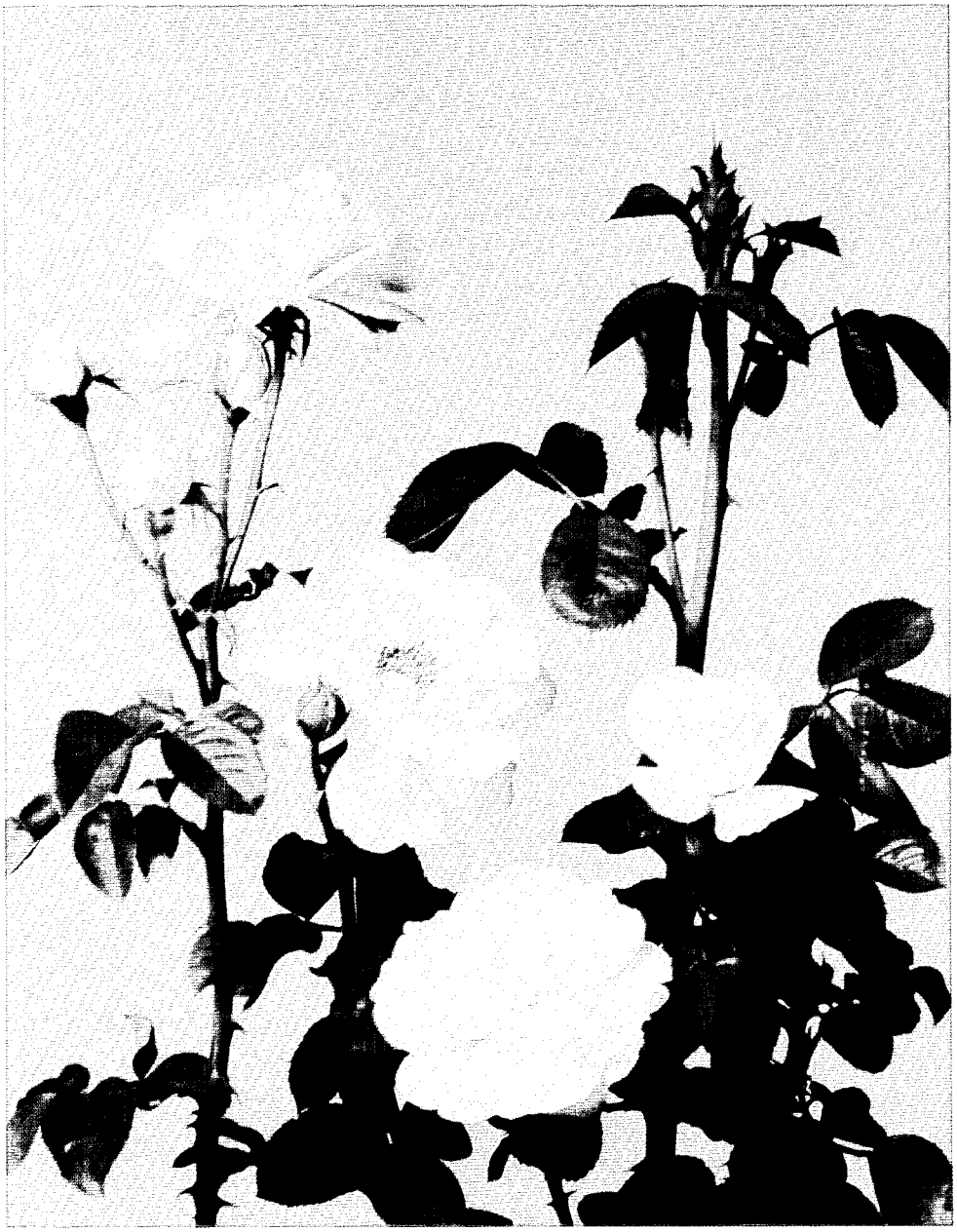
Inventor.
D. L. Armstrong
By: Robb & Robb
Attorneys.

United States Patent Office

Plant Pat. 2,849
Patented Dec. 3, 1968

2,849

ROSE PLANT

David L. Armstrong, Ontario, Calif., assignor to Armstrong Nurseries, Inc., Ontario, Calif., a corporation of California

Filed June 14, 1967, Ser. No. 646,132
1 Claim. (Cl. Plt.—24)

The present invention relates to a new and distinct variety of rose plant of the floribunda (hybrid polyantha) class, which was originated by me by crossing the rose variety known as "Fandango" (Plant Patent No. 894) with the variety known as "Pinocchio" (Plant Patent No. 484), the former being the seed parent and the latter being the pollen parent.

The new variety resulted from an extensive breeding program having for its objective to produce improved large-flowered floribunda rose varieties which bear flowers of various colors. This objective was fully achieved, as evidenced by the following unique combination of characteristics which are outstanding in the new variety and which distinguish it from its parents, as well as from all other varieties of which I am aware:

(1) A vigorous plant having an attractive, semi-upright, bushy and well-foliaged plant habit;

(2) A very floriferous habit, with the flowers usually borne in small clusters on short to medium length stems typical of a good floribunda habit;

(3) Excellent urn-shaped buds and an attractive high-centered open flower form;

(4) Medium sized flowers of quite double petalage; and (5) A distinctive light to medium yellow flower color which remains attractive at all times.

In comparison with its seed parent, "Fandango," the new variety has a less vigorous but more bushy plant habit, its flowers are usually borne in small clusters contrary to the usually single flowers of this parent; the flowers are considerably more double; and the flowers are yellow in color instead of red like those of this parent.

As compared with its pollen parent, "Pinocchio," the new variety bears larger flowers than those of this parent; and the flowers are yellow in color instead of pink or pink blended like the flowers of this parent.

Asexual reproduction of my new variety by budding, as performed at Ontario, Calif., shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Robert F. Wilson's Horticultural Colour Chart (hereinafter abbreviated (W)) and Robert Ridgway's Color Standards and Nomenclature (hereinafter abbreviated (R)), as indicated:

Type: Bush, outdoor; seedling; for cut flowers and for garden decoration.

Class: Floribunda (hybrid polyantha).

Breeding: Seedling.

*Seed parent.*—"Fandango."

*Pollen parent.*—"Pinocchio."

Propagation: Holds its distinguishing characteristics through succeeding propagations by budding.

*Flower*

Locality where grown and observed: Ontario, Calif.

Flowers borne: Sometimes singly, but usually five or more to stem; in irregular clusters; on strong, short to medium length stems.

Quantity of bloom: Abundant, outdoors.

Continuity: Nearly continuous during growing season.

Fragrance: From slight to moderate.

Bud:

*Peduncle.*—From short to average length; average caliper; erect; usually smooth; with several to many stipitate glands and none to few small prickles. Color—near Lime Green, Plate XXXI (R), overlaid with near Ocher Red, Plate XXVII (R) on side exposed to sun.

*Before calyx breaks.*—Size—from small to medium. Form short; ovoid.

*As calyx breaks.*—Color—between Fire Red, Plate 15/2, page 15 (W) and Poppy Red, Plate 16/2, page 16 (W).

*Sepals.*—Inner surface—with fine, wooly tomentum. Outer surface usually smooth. Alternate margins lined with fine, wooly tomentum. Other margins with several to many small stipitate glands and small, slender foliaceous parts.

*As first petal opens.*—Size—from small to average. Form short; ovoid; usually urn-shaped. Color: Outside—near Buttercup Yellow, Plate 5/2, page 5 (W), with area exposed to sun longer near Fire Red, Plate 15/3, page 15 (W); inside—near Buttercup Yellow, Plate 5/2, page 5 (W), with small area at base of petal near attachment near Aureolin, Plate 3, page 3 (W).

*Opening.*—Opens up well; is not retarded or prevented from opening by cold, hot, wet or dry weather.

Bloom:

*Size (when fully open).*—Average; from 3¼ inches to 4 inches.

*Petalage.*—Double; from 30 to 40 petals, plus 12 to 15 petaloids; arranged irregularly.

*Form.*—High-centered at first, but becoming cupped to high-centered; petals being at first tightly cupped, with tips rolled outward, but later becoming loosely flat to cupped at maturity, with tips slightly rolled outward.

Petals:

*Texture.*—Medium thickness.

*Appearance.*—Inside—satiny. Outside satiny.

*Shape.*—Outside—broadly obovate, with apex flat to rounded and usually with 1 or 2 notches. Intermediate—obovate, with apex rounded and usually with 1 or 2 notches. Inside—obovate, with apex rounded and usually with 1 or 2 notches.

This description of a newly opened flower was made from a rose grown outdoors during the month of August at Ontario, Calif.:

*Color.*—Outer petal: outside surface—near Lemon Yellow, Plate 4/3, page 4 (W), blending with near Aureolin, Plate 3/1, page 3 (W) toward base of petal; inside surface—near Aureolin, Plate 3/3, page 3 (W), blending with near Canary Yellow, Plate 2/1, page 2 (W), toward base of petal. Intermediate petal: outside surface—near Aureolin, Plate 3/2, page 3 (W), blending with near Canary Yellow, Plate 2/1, page 2 (W) toward base of petal; inside surface—same as outside surface. Inner petal: outside surface—near Aureolin, Plate 3/2, page 3 (W), blending with near Canary Yellow, Plate 2, page 2 (W) toward base of petal; inside surface—same as outside surface.

This description was made from a rose that was open for three days outdoors during the month of August at Ontario, Calif.:

*Color.*—Outer petal: outside surface—near Mimosa Yellow, Plate 602/3, page 143 (W), blending with near Primrose Yellow, Plate 601/2, page 65 (W) toward base of petal; inside surface—near Mimosa Yellow, Plate 602/3, page 143 (W), blending with near Primrose Yellow, Plate 601/1, page 65 (W) toward base of petal. Inner petal: outside surface—same as outer petal; inside surface—same as outer petal.

*General color effect.*—Newly opened flower—from Aureolin, Plate 3/3, page 3 (W) to Lemon Yellow, Plate 4/2, page 4 (W). Three days open—near Mimosa Yellow, Plate 602/3, page 143 (W), with center of flower near Empire Yellow, Plate 603/1, page 66 (W).

*Behavior.*—Drop off cleanly; not particularly affected by cold, hot, wet or dry weather.

*Flower longevity.*—On bush in garden—3 or 4 days in November. Cut roses grown outdoors and kept at living-room temperatures—2 or 3 days in November.

*Reproductive organs*

Stamens: From average number to many; arranged regularly about pistils; a few mixed with petaloids.

Filaments: Medium length (from 5 mm. to 12 mm. long); most with anthers. Color—near Buttercup Yellow, Plate 5, page 5 (W).

Anthers: From small to medium size; all open approximately at once. Color: upper side—margins near Saffron Yellow, Plate 7/1, page 7 (W), with remainder near Canary Yellow, Plate 2/3, page 2 (W); under side—margins near Saffron Yellow, Plate 7/1, page 7 (W), with remainder near Canary Yellow, Plate 2/3, page 2 (W).

Pollen: Moderately abundant. Color—near Cadmium Orange, Plate 8/1, page 8 (W).

Pistils: Average number (approximately 50).

Styles: Uneven; from short to average length; thin; bunched. Color—upper ½ near Carmine, Plate 21/3, page 21 (W), with remainder near Primrose Yellow, Plate 601/3, page 65 (W).

Stigma: Color—near Straw Yellow, Plate 604/2, page 67 (W).

Ovaries: Usually all enclosed in calyx.

Hips: Average length; globular; rough; walls thick and fleshy. Color (mature)—from Apricot Orange, Plate XIV (R) to Rood's Brown, Plate XXVIII (R).

Sepals: Falling soon; medium length; straight. Color: inside—near Vetiver Green, Plate XLVII (R); outside—near Light Yellowish-Olive, Plate XXX (R).

Seeds: From average number to many (from 25 to 40); small.

*Plant*

Foliage:

*Leaves.*—Compound of usually 3 to 7 leaflets; abundant; medium size; leathery; semi-glossy.

*Leaflets.*—Shape—broadly oval. Apex usually acute, but some round. Base round. Margin simply serrate.

*Color.*—Mature: upper surface—near Deep Dull Yellow-Green (2), Plate XXXII (R); under surface—near Chromium Green, Plate XXXII (R). Young: upper surface—near Light Bice Green, Plate XVII (R); under surface—between Apple Green, Plate XVII (R) and Light Bice Green, Plate XVII (R).

*Rachis (the supporting stem of the compound leaf).*—Average size.

Upper side—Grooved; with several to many small stipitate glands on edges. Under side—smooth; with none to few stipitate glands and few small prickles.

*Stipules.*—Medium length; medium width; with short points turning out at an angle of more than 45°.

*Disease resistance.*—Better than average resistance to mildew, as determined by comparison with other floribunda (hybrid polyantha) varieties grown under field and garden conditions at Ontario, Calif.

Growth:

*Habit.*—Bushy; upright-spreading; much-branched.

*Growth.*—From free to vigorous.

*Canes.*—Medium caliper.

*Main stems.*—Color—near Light Cress Green, Plate XXXI (R). Large prickles—from several to many; from medium length to long; hooked slightly downward; with medium length to long, narrow base; color—near Russet, Plate XV (R). Small prickles—none. Hairs—none.

*Branches.*—Color—near Biscay Green, Plate XVII (R). Large prickles—from several to many; medium length; hooked slightly downward; with medium length, narrow base; color—near Cacao Brown, XXVIII (R). Small prickles—none. Hairs—none.

*New shoots.*—Color—near Apple Green, Plate XVII (R), overlaid with near Prussian Red, Plate XXVII (R) on side exposed to sun. Large prickles—several; short; hooked slightly downward; with medium length, narrow base; color—near Mineral Red, Plate XXVII (R). Small prickles—none. Hairs—none.

I claim:

1. A new and distinct variety of rose plant of the floribunda (hybrid polyantha) class, substantially as herein shown and described, characterized particularly as to novelty by the unique combination of a vigorous plant having an attractive, semi-upright, bushy and well-foliaged plant habit, a very floriferous habit, with the flowers usually borne in small clusters on short to medium length stems typical of a good floribunda habit, excellent urn-shaped buds and an attractive high-centered open flower form, medium sized flowers of quite double petalage, and a distinctive light to medium yellow flower color which remains attractive at all times.

No references cited.

ROBERT E. BAGWILL, *Primary Examiner.*